(12) United States Patent
Yamaguchi

(10) Patent No.: US 6,642,515 B1
(45) Date of Patent: Nov. 4, 2003

(54) METHOD AND APPARATUS FOR ELECTROSPRAY MASS SPECTROMETRIC ANALYSIS

(75) Inventor: Kentaro Yamaguchi, Chiba (JP)

(73) Assignee: Japan Science and Technology Corporation (JP)

( * ) Notice: Subject to any disclaimer, the term of this patent is extended or adjusted under 35 U.S.C. 154(b) by 0 days.

(21) Appl. No.: 09/936,938

(22) PCT Filed: Mar. 28, 2000

(86) PCT No.: PCT/JP00/01890
§ 371 (c)(1),
(2), (4) Date: Sep. 20, 2001

(87) PCT Pub. No.: WO00/60641
PCT Pub. Date: Oct. 12, 2000

(30) Foreign Application Priority Data

Mar. 30, 1999 (JP) ............................................. 11-87356

(51) Int. Cl.[7] ................................................ H01J 49/10
(52) U.S. Cl. ........................................ 250/288; 250/281
(58) Field of Search ................................ 250/281–288, 250/424–425, 423 R

(56) References Cited

FOREIGN PATENT DOCUMENTS

| EP | 0249424 | 8/1987 |
|----|---------|--------|
| JP | 50-138085 | 4/1949 |
| JP | 7-161322 | 6/1995 |
| JP | 11-64283 | 3/1999 |
| JP | 11-64288 | 3/1999 |

*Primary Examiner*—John R. Lee
*Assistant Examiner*—Christopher M. Kalivoda
(74) *Attorney, Agent, or Firm*—Lorusso, Loud & Kelly

(57) ABSTRACT

The invention is provides a method and an apparatus for performing electrospray ionization mass spectrometric analysis, which method can exactly analyze a mass of a molecular ion or a fragment ion of an unstable organometallic complex or a polymeric organic compound. The method includes cooling a sample to be analyzed which contains a solvent and is caused to flow out from a spray small-diameter tube with an inert gas for low temperature vaporization (A), and carrying out ionization and mass spectrometric analysis of the sample to be analyzed while cooling a chamber (7) for removing a solvent or an ion source shield (8) with liquid nitrogen.

8 Claims, 5 Drawing Sheets

FIG. 3 (a)
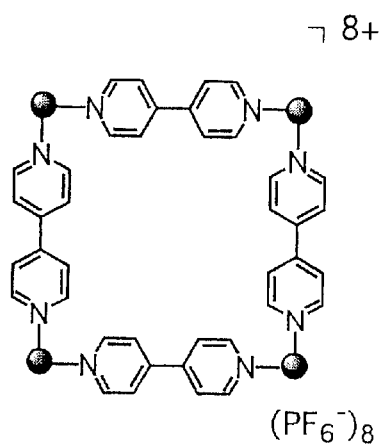
(PF$_6^-$)$_8$
FIG. 3 (b)
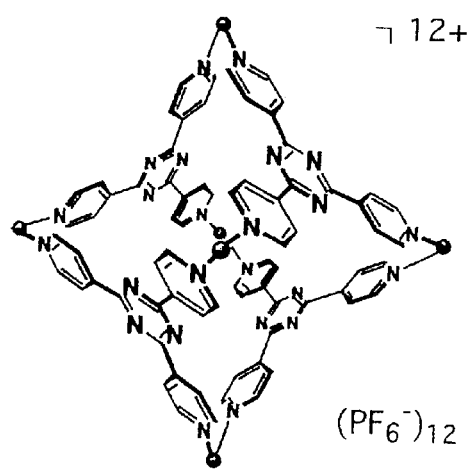
(PF$_6^-$)$_{12}$
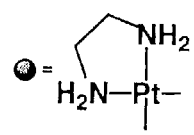

METHOD AND APPARATUS FOR ELECTROSPRAY MASS SPECTROMETRIC ANALYSIS

TECHNICAL FIELD

The present invention relates to a method for performing electrospray mass spectrometric analysis and to an apparatus for performing the analysis.

BACKGROUND ART

Conventionally techniques related to such a technical field are described, for example, in the following literature:

(1) F. Bitsch, C. O. D. Buchecker, A. K. Khemiss, J. P. Sauvage, A. V. Dorsselaer, *J. Am. Chem. Soc.* 1991, 113, 4023–4025;

(2) D. C. Buchecker, E. Leize, J. F. Nierengarten, J. P. Sauvage, A. V. Dorsselaer, *J. Chem. Soc., Chem. Commun.* 1994, 2257–2258; and (3) D. Whang, K. M. Park, J. Heo, P. Ashton, K. Kim, *J. Am. Chem. Soc.* 1998, 120, 4899–4900.

Liquid-introduction electrospray ionization (ESI) apparatuses have been developed so as to analyze molecular structures of biopolymers such as proteins; organometallic complexes; etc.

Organometallic compounds—including highly-ordered supermolecules containing a transition metal that are formed through self-assembly—have been of interest [See (1) F. Bitsch, C. O. D. Buchecker, A. K. Khemiss, J. P. Sauvage, A. V. Dorsselaer, *J. Am. Chem. Soc.* 1991, 113, 4023–4025; (2) D. C. Buchecker, E. Leize, J. F. Nierengarten, J. P. Sauvage, A. V. Dorsselaer, *J. Chem. Soc., Chem. Commun.* 1994, 2257–2258; (3) D. Whang, K. M. Park, J. Heo, P. Ashton, K. Kim, *J. Am. Chem. Soc.* 1998, 120, 4899–4900; and (4) M. Fujita, K. Ogura, *Coord. Chem. Rev.*; 1996, 148, 249–264.].

These compounds have been analyzed in terms of characteristics and detailed molecular structure, mainly through X-ray crystallography and nuclear magnetic resonance (NMR) spectroscopy.

DISCLOSURE OF THE INVENTION

However, single crystals having sufficient purity for allowing precise X-ray crystallographic structure analysis are generally difficult to obtain. For example, when molecules dissolved in the solution undergo rapid intertransformation or contain metallic atoms exhibiting supermagnetism, NMR spectroscopy is not useful for characterizing molecules that are in a dissolved state. Mass spectrometry is another candidate method for effectively analyzing such metal complexes in the solution state. However, only a few cases of effective mass spectrometric analysis have been reported (see the aforementioned published literature (1) to (3)). Since these metal complexes are generally unstable against impact or heat for causing ionization, such poor stability of the complexes poses a problem, even when milder ionization through fast atom bombardment (FAB) or electrospray ionization (ESI) is employed.

In view of the foregoing, an object of the present invention is to provide a method for performing electrospray ionization mass spectrometric analysis, which method is capable of precisely analyzing the characteristics of unstable organometallic complexes. Another object of the invention is to provide an apparatus for performing the analysis.

To achieve the above objects, the present invention provides the following.

[1] a method for performing electrospray mass spectrometric analysis, characterized by comprising atomizing a sample solution to be analyzed which contains a solvent and is caused to flow out from a small-diameter tube for spraying while the sample solution is cooled by means of a gas for vaporization; and ionizing the atomized sample solution to be analyzed while a chamber for removing a solvent and an ion source shield are cooled, to thereby perform mass spectrometric analysis of the sample.

[2] a method for performing electrospray mass spectrometric analysis as described in [1], wherein the gas for vaporization and the ion source shield are maintained at low temperature within the range of liquid nitrogen temperature to room temperature.

[3] a method for performing electrospray mass spectrometric analysis as described in [1], wherein the sample to be analyzed is an organic compound.

[4] a method for performing electrospray mass spectrometric analysis as described in [1], wherein the gas for vaporization is a nebulizer gas.

[5] a method for performing electrospray mass spectrometric analysis as described in [1], wherein the gas for vaporization is an inert gas such as nitrogen gas.

[6] a method for performing electrospray ionization mass spectrometric analysis as described in [1], wherein water or a non-polar organic solvent (e.g., $H_2O$, $CH_3CN$, $CHCl_3$) is used as the solvent, so as to perform molecular structure analysis.

[7] an apparatus for performing electrospray mass spectrometric analysis, characterized by comprising a small-diameter tube for spraying and for causing to flow out a sample solution to be analyzed containing a solvent; a sheath tube which is co-axially provided with the tube for spraying and allows passage of a gas for cooling; a chamber for removing a solvent and an ion source shield which are cooled; and a mass spectrometer for ionizing by use of the solvent and performing mass analysis of a sample to be analyzed; wherein an ion source formed through electrospraying is employed while the ion source is cooled by spraying liquid nitrogen directly to a chamber for removing a solvent and to an ion source shield.

[8] an apparatus for performing electrospray mass spectrometric analysis as described in [7], wherein the gas for cooling is introduced into the sheath tube after treatment in an apparatus for cooling an inert gas.

BRIEF DESCRIPTION OF THE DRAWINGS

FIG. 3 shows chemical structures of self-assembly organometallic complexes which were subjected to low-temperature electrospray mass spectrometric analysis according to the embodiment.

BEST MODES FOR CARRYING OUT THE INVENTION

A mode for carrying out the invention will next be described in detail.

In order to detect molecular ions of an organometallic complex which is unstable and/or contains an ion, the present invention provides a practical low-temperature ionization method by employing low-temperature spraying; liquid introduction and electrospraying; or ion spraying (IS).

Figure 1:
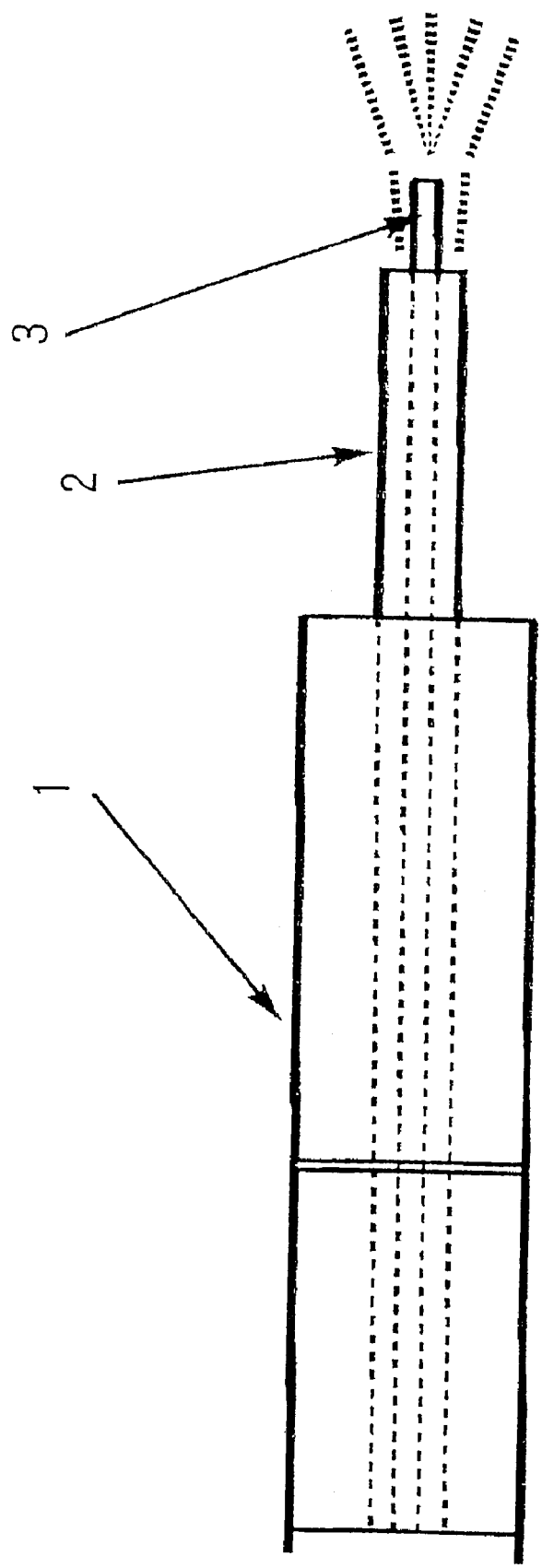
FIG. 1 shows a schematic view of a low-temperature electrospray probe according to one embodiment of the present invention.
Figure 2:
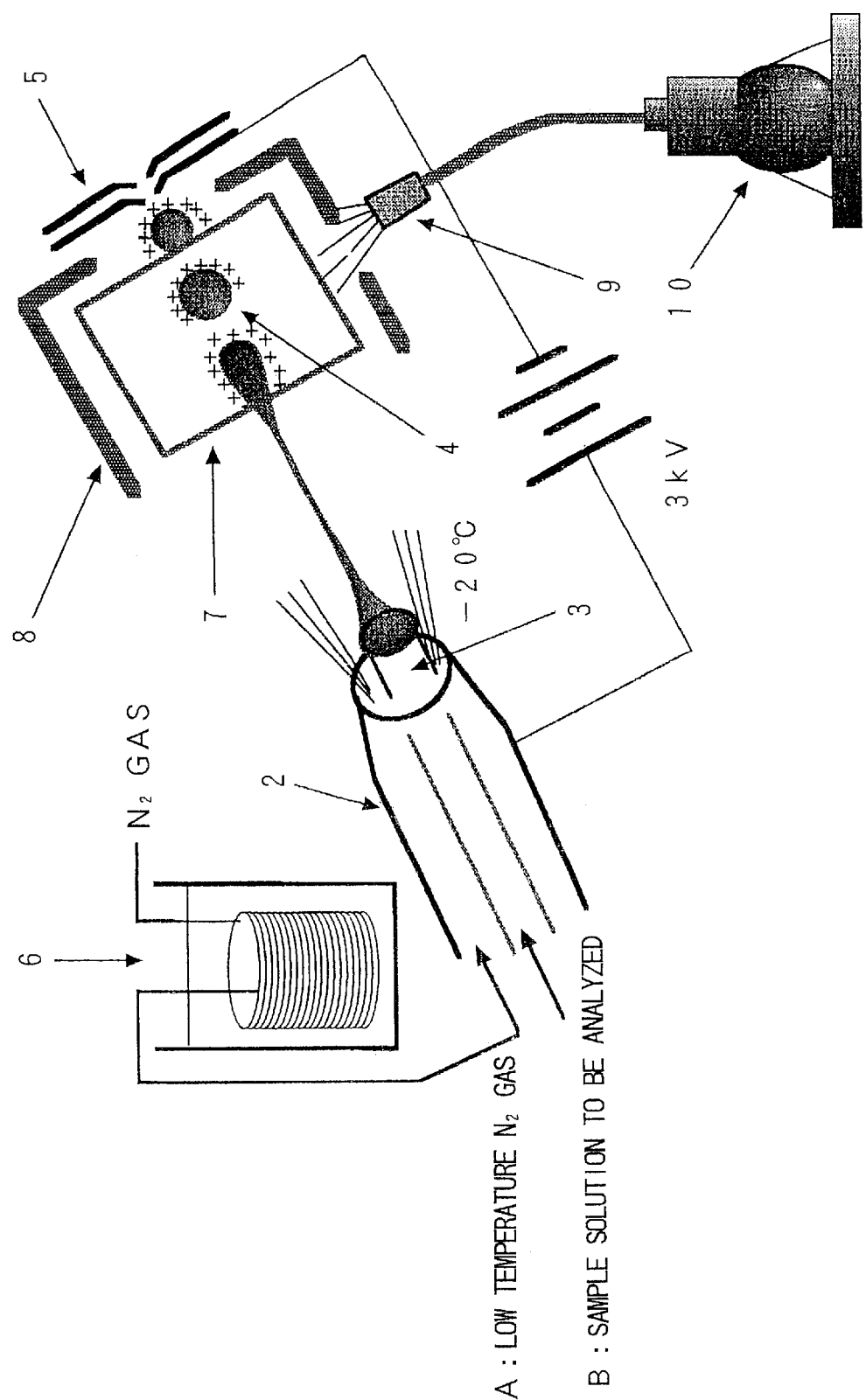
FIG. 2 shows a schematic view of an ionization step employing electrospraying at low temperature according to the embodiment.

FIG. 1 shows a schematic view of a low-temperature electrospray probe according to one embodiment of the present invention, and FIG. 2 shows a schematic view of a feature of ionization by electrospraying.

In FIGS. 1 and 2, reference numeral 1 represents a probe for performing low-temperature electrospray ionization; reference numeral 2 represents a sheath tube; reference numeral 3 represents a capillary for performing spray ionization (a small-diameter tube for introducing a sample solution); reference numeral 4 represents charged droplets; reference numeral 5 represents an electrode connecting to a mass spectrometer and for transferring ions; reference numeral 6 represents an apparatus for cooling a (dry) gas ($N_2$) for vaporization; reference numeral 7 represents a chamber for removing a solvent; reference numeral 8 represents an ion source shield; reference numeral 9 represents a nozzle for spraying liquid nitrogen; and reference numeral 10 represents liquid nitrogen.

Specifically, $N_2$ gas is cooled to approximately $-100°$ C. by means of the apparatus 6 for cooling a gas for vaporization, and a sample solution to be analyzed is atomized at approximately $-20°$ C. In FIG. 2, reference symbol A represents a low-temperature $N_2$ gas and reference symbol B represents a sample solution to be analyzed.

As shown in FIG. 2, a gas (nebulizer gas) for vaporization; e.g., nitrogen, is passed through the apparatus 6 for cooling a gas 6 (nitrogen) for vaporization and, subsequently, is introduced into an electrospray, so as to maintain at a low temperature the capillary 3 and the spray itself. During ionization, the chamber 7 for removing a solvent and the ion source shield 8 are maintained at approximately $15°$ C. or less by being sprayed with liquid nitrogen from the nozzle 9 for spraying liquid nitrogen. The following experiments were carried out by use of a sector-type mass spectrometer connecting to ESI sources.

The low-temperature ESI-MS was operated in a cation mode, to thereby perform mass analysis of self-assembly metal complexes. Typical examples of the complexes include "molecular squares" as shown in FIG. 3(a) [See (A) M. Fujita, J. Yazaki, K. Ogura, K., *J. Am. Chem. Soc.* 1990, 112, 5645–5647 and (B) M. Fujita, O. Sasaki, T. Mitushashi, T. Fujita, K. Yamaguchi, K. Ogura, *J. Chem. Soc., Chem. Commun*, 1996, 1535–1536.] and "adamantanoid cages" as shown in FIG. 3(b) [See M. Fujita, D. Oguro, M. Miyazawa, H. Oka, K. Yamaguchi, K. Ogura, *Nature*, 1995, 378, 469–471.].

Figure 4:
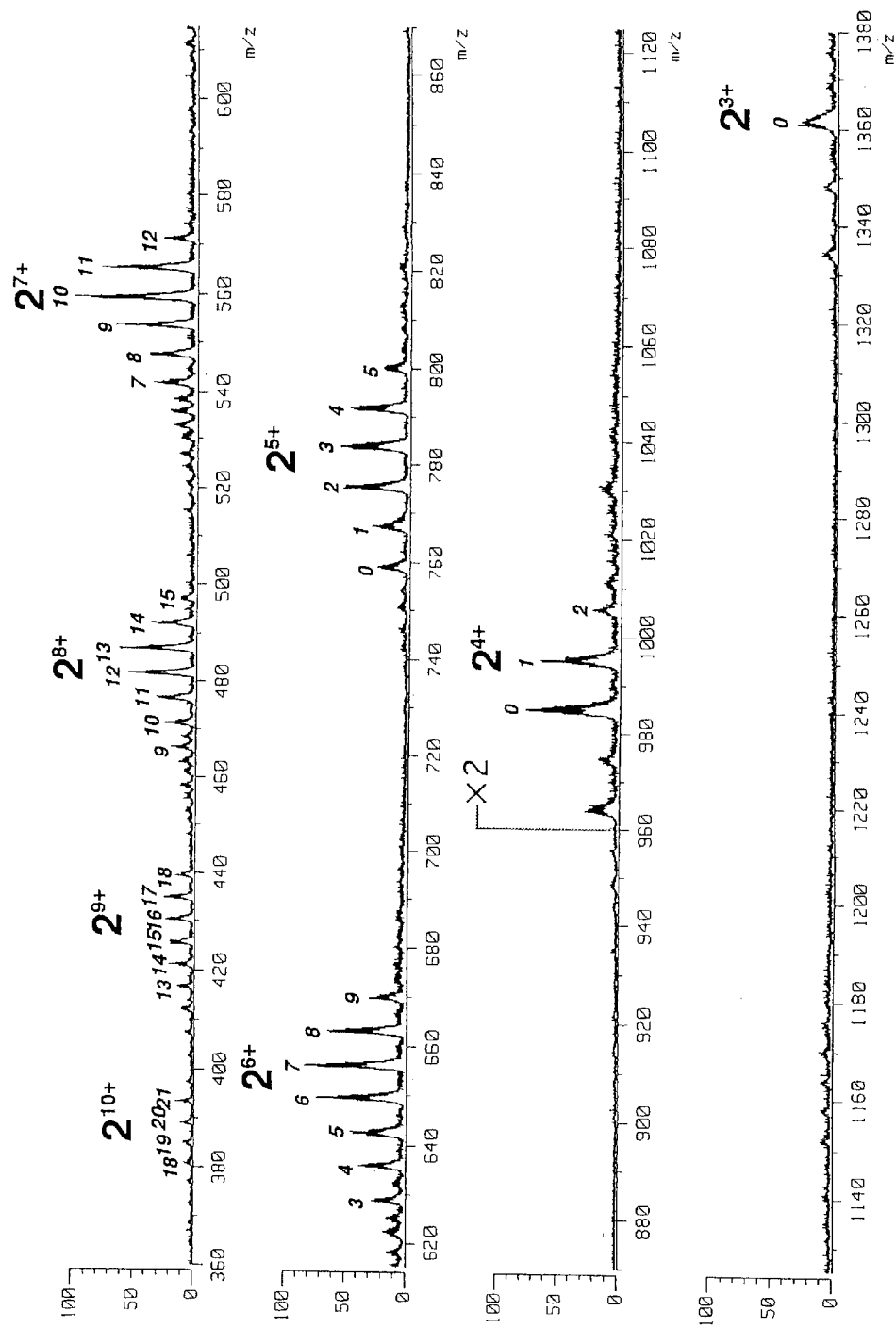
FIG. 4 shows a mass spectrum indicating typical analytical results (Compound b) obtained in accordance with the present invention.

Analysis of these compounds leads to the following optimum analysis conditions. Briefly, (1) Ion source: A sheath gas ($N_2$) at $-20°$ C. or lower and a non-solvated plate at $15°$ C. were selected; (2) Solvent: $CH_3CN$ was the optimum solvent for such molecules; and (3) Detection sensitivity of counter ions: The sensitivity increased in the order of $NO_3^- < BF_4^- < PF_6^-$. In addition, the central transition metal atom contained in a molecule of these compounds was also investigated in terms of adaptability to the mass analysis. As a result, Pt(II) complexes were found to exhibit the highest sensitivity in this analysis. FIG. 4 (case 2) shows typical results of analysis, indicating that multiply-charged polyvalent molecular ions (+3 to +10) are clearly observed simultaneously with a number of solvent ($CH_3CN$) molecules (up to 21). More interestingly, the number of $CH_3CN$ molecules increased with the charge of the ion. This phenomenon was also observed for compounds shown in FIGS. 3(a) and 3(b).

From the foregoing phenomenon, which had never before been confirmed, the inventors have found an important application of low-temperature spraying.

Specifically, highly charged droplets which have been formed by mixing molecules to be analyzed with a solvent and atomizing the resultant mixture from a small-diameter tube are readily polarized. Thus, counter ions corresponding to the cations are readily plucked out. This easy plucking of the counter ions is assisted by solvation. Since the electrospray ionization (ESI) mechanism which has previously been proposed essentially requires a step of evaporating a solvent, the spray must be heated. In contrast, in the low-temperature electrospray ionization mechanism in accordance with the present invention, removal of a solvent which is closely related to ionization must be suppressed to the utmost extent. The reason for this is that a polar solvent exhibits a higher dielectric constant at lower temperature.

Figure 5:
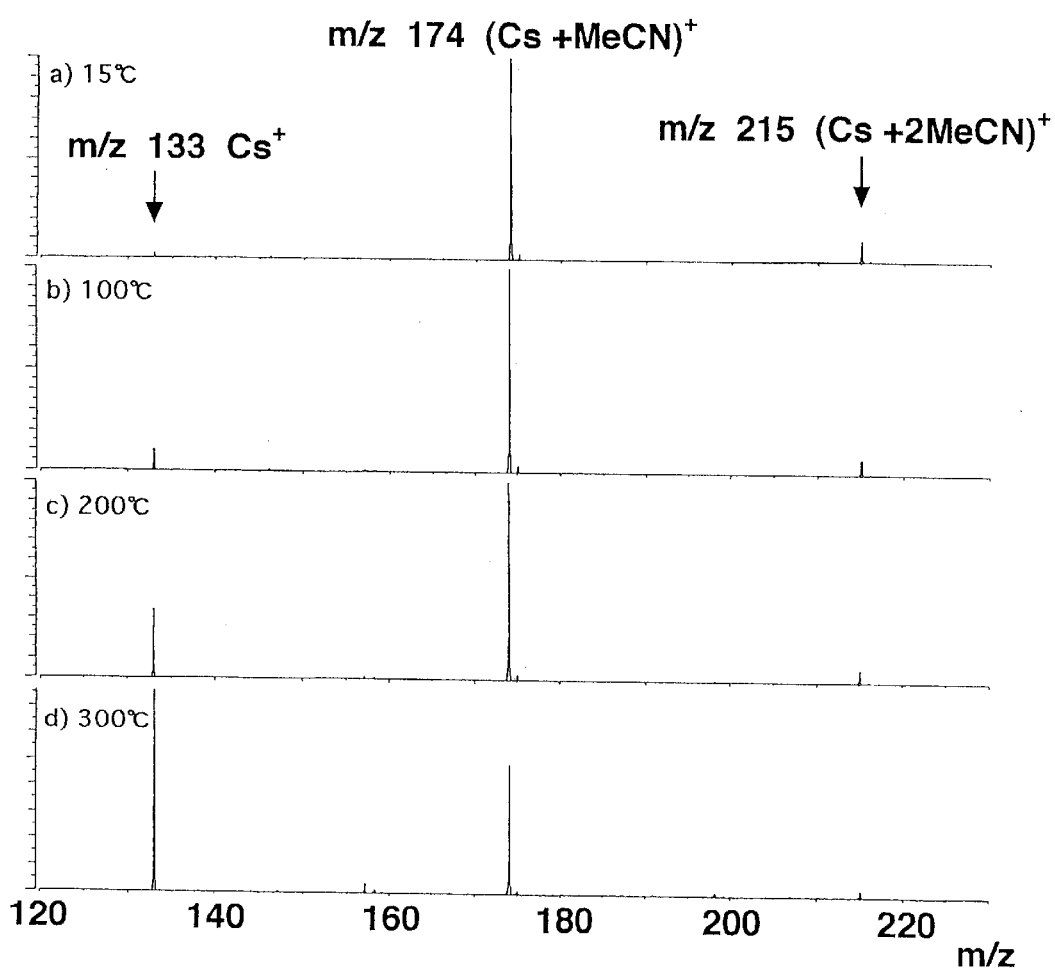
FIG. 5 shows charts indicating the dependency on temperature of the intensity ratio of $[Cs]^+$ to $[Cs+CH_3CN]^+$ obtained by subjecting a solution of CsI dissolved in $CH_3CN$ to analysis according to the embodiment.

The above theoretical mechanism can be confirmed by a simplified experiment on ESI for detecting cations by use of NaCl, KI, or CsI. FIG. 5 shows the dependency of the ion intensity ratio of $[Cs]^+$ to that of $[Cs+CH_3CN]^+$ on temperature, when a sample containing CsI dissolved in $CH_3CN$ is subjected to ESI.

When ESI was carried out at $300°$ C., the intensity of $[Cs]^+$ was higher than that of $[Cs+CH_3CN]^+$, whereas when ESI was carried out at $15°$ C., the intensity of $[Cs+CH_3CN]^+$ predominated.

The above results show the importance of solvation observed at low temperature. Thus, the present inventors applied this model mechanism—"solvation-assisted counter ion plucking" (SACP)—to studies on ionization of ionic samples to be analyzed. According to this mechanism, polyvalent ions which are formed through solvation of Compounds (a) and (b) shown in FIG. 3 decrease with increasing ionization temperature. Therefore, through low-temperature electrospray ionization according to the present invention and based on the SACP mechanism, polyvalent ions solvated with corresponding numbers of solvent molecules are considered to be formed.

In other words, the present invention provides a performance-enhanced apparatus for performing electrospray ionization in a cooled state and a method of performing mass structure analysis of unstable self-assembly metal complexes on the basis of molecular weight measurement making use of the apparatus.

According to the present invention, solvated polyvalent molecular ions can be clearly detected. Thus, the present invention has been proven to be effective for analysis of such organometallic compounds.

The aforementioned SACP theoretical mechanism has been proposed as a theory which can describe the mechanism of forming polyvalent molecular ions concomitant with solvation during low-temperature electrospray ionization in accordance with the present invention.

As described above, the present invention enables precise analysis of molecular structure of organometallic compounds.

The present invention is not limited to the above-described embodiment. Numerous modifications and variations of the present invention are possible in light of the spirit of the present invention, and are not excluded from the scope of the present invention.

As described in detail hereinabove, the present invention provides the following effects.

(1) The low-temperature electrospray ionization apparatus according to the present invention attains exact mass analysis of molecular ions and fragment ions of unstable organometallic compounds and polymeric organic compounds.

(2) The mechanism of ionization according to the invention is based on solvation which is caused by an increase, due to cooling, in dielectric constant of the corresponding solvent, and a number of the thus-formed solvated molecular ions are observed.

(3) Modifying the solvent and samples to be analyzed may enable analysis of electrically neutral species.

INDUSTRIAL APPLICABILITY

The method and apparatus of the present invention for performing electrospray mass spectrometric analysis are suitable for mass spectrometric analysis of unstable organic compounds, which analysis has previously been impossible or difficult.

What is claimed is:

1. A method for performing electrospray mass spectrometric analysis, characterized by comprising atomizing a sample solution to be analyzed which contains a solvent and is caused to flow out from a small-diameter tube for spraying while the sample solution is cooled by means of a gas for vaporization; and ionizing the atomized sample solution to be analyzed while a chamber for removing a solvent and an ion source shield are cooled, to thereby perform mass spectrometric analysis of the sample.

2. A method for performing electrospray mass spectrometric analysis as described in claim 1, wherein the gas for vaporization and the ion source shield are maintained at low temperature within the range of liquid nitrogen temperature to room temperature.

3. A method for performing electrospray mass spectrometric analysis as described in claim 1, wherein the sample to be analyzed is an organic compound.

4. A method for performing electrospray mass spectrometric analysis as described in claim 1, wherein the gas for vaporization is a nebulizer gas.

5. A method for performing electrospray mass spectrometric analysis as described in claim 1, wherein the gas for vaporization is an inert gas such as nitrogen gas.

6. A method for performing electrospray ionization mass spectrometric analysis as described in claim 1, wherein water or a non-polar organic solvent (e.g., $H_2O$, $CH_3CN$, $CHCl_3$) is used as the solvent, so as to perform molecular structure analysis.

7. An apparatus for performing electrospray mass spectrometric analysis, characterized by comprising (a) a small-diameter tube for spraying and for causing to flow out a sample solution to be analyzed containing a solvent;

(b) a sheath tube which is co-axially provided with the tube for spraying and allows passage of a gas for cooling;

(c) a chamber for removing a solvent and an ion source shield which are cooled; and (d) a mass spectrometer for ionizing by use of the solvent and performing mass analysis of a sample to be analyzed;

(e) wherein an ion source formed through electrospraying is employed while the ion source is cooled by spraying liquid nitrogen directly to a chamber for removing a solvent and to an ion source shield.

8. An apparatus for performing electrospray mass spectrometric analysis as described in claim 7, wherein the gas for cooling is introduced into the sheath tube after treatment in an apparatus for cooling an inert gas.

* * * * *